(12) United States Patent
Carey

(10) Patent No.: US 8,201,559 B2
(45) Date of Patent: Jun. 19, 2012

(54) METHOD OF SURGICAL REPAIR OF VAGINA DAMAGED BY PELVIC ORGAN PROLAPSE AND PROSTHETIC MATERIALS AND DEVICES SUITABLE FOR USE THEREIN

(75) Inventor: Marcus P. Carey, Eltham (AU)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 12/609,914

(22) Filed: Oct. 30, 2009

(65) Prior Publication Data

US 2010/0154801 A1 Jun. 24, 2010

Related U.S. Application Data

(62) Division of application No. 10/534,930, filed as application No. PCT/AU2003/001494 on Nov. 12, 2003, now Pat. No. 7,628,155.

(30) Foreign Application Priority Data

Nov. 15, 2002 (AU) ................................ 2002952693
Sep. 10, 2003 (AU) ................................ 2003904937

(51) Int. Cl.
*A61F 6/06* (2006.01)
*A61F 2/02* (2006.01)
*A61F 2/00* (2006.01)

(52) U.S. Cl. .......... 128/834; 600/37; 600/30; 623/23.72
(58) Field of Classification Search .................. 128/898, 128/834; 600/37, 29, 30; 206/363, 438; 442/46, 49; 606/151, 119; 623/23.72
See application file for complete search history.

(56) References Cited

U.S. PATENT DOCUMENTS

| 2,475,071 A | 7/1949 | Young |
| 4,307,716 A | 12/1981 | Davis |
| 4,685,447 A * | 8/1987 | Iversen et al. ................. 128/899 |
| 5,840,011 A | 11/1998 | Landgrebe et al. |
| 6,216,698 B1 | 4/2001 | Regula |
| 6,575,897 B1 | 6/2003 | Ory et al. |
| 6,599,235 B2 | 7/2003 | Kovac |
| 6,758,853 B2 * | 7/2004 | Kieturakis et al. ............ 606/190 |
| 6,981,983 B1 | 1/2006 | Rosenblatt et al. |
| 7,011,688 B2 * | 3/2006 | Gryska et al. .............. 623/23.72 |
| 7,087,065 B2 * | 8/2006 | Ulmsten et al. ................ 606/151 |
| 7,594,921 B2 * | 9/2009 | Browning ...................... 606/151 |
| 2002/0028980 A1 | 3/2002 | Thierfelder et al. |

(Continued)

FOREIGN PATENT DOCUMENTS

AU 2002952693 11/2002

(Continued)

OTHER PUBLICATIONS

English translation of Japanese Examination report dated Jul. 8, 2008 in International Patent Application No. 2004-570245.

(Continued)

*Primary Examiner* — Patricia Bianco
*Assistant Examiner* — Tarla Patel

(57) ABSTRACT

A method for repairing a vaginal wall (35) which has been damaged by one or more prolapsed pelvic organs said method including: (a) mobilizing the vaginal epithelium off the underlying fascia of at least a portion of the damaged vaginal wall; (b) positioning a prosthetic material (36) over the exposed fascia; (c) re-fixing the vaginal epithelium over the prosthetic material (36) and the fascia; and thereafter (d) locating an intra-vaginal splint into the vagina.

16 Claims, 6 Drawing Sheets

U.S. PATENT DOCUMENTS

| | | | |
|---|---|---|---|
| 2002/0072694 A1 | 6/2002 | Snitkin et al. | |
| 2002/0083949 A1 | 7/2002 | James | |
| 2005/0283189 A1* | 12/2005 | Rosenblatt | 606/216 |
| 2007/0088189 A1 | 4/2007 | Levy | |

FOREIGN PATENT DOCUMENTS

| | | |
|---|---|---|
| AU | 2003 904937 | 9/2003 |
| BY | 2 664 | 3/1999 |
| CA | 331100 | 3/1933 |
| CA | 600904 | 7/1960 |
| DE | 9104155 | 6/1991 |
| EP | 084755 | 8/1983 |
| FR | 2785521 | 5/2000 |
| JP | 2001-511685 | 8/1998 |
| JP | 2001-51734 | 4/1999 |
| RU | 2 209 605 C2 | 7/2001 |
| RU | 2 196 519 | 1/2003 |
| RU | 2 232 562 | 7/2004 |
| WO | WO 96/01084 A | 1/1996 |
| WO | WO 96/03091 A | 2/1996 |
| WO | WO 98/35632 | 8/1998 |
| WO | WO 99/16381 | 4/1999 |
| WO | WO 01/06951 A1 | 2/2001 |
| WO | WO 02/078552 A1 | 10/2002 |
| WO | WO 02/078568 A1 | 10/2002 |
| WO | WO 03/028585 A2 | 4/2003 |

OTHER PUBLICATIONS

Boyles S.H. et al., "Procedures for Pelvic Organ Prolapse in the United States, 1979-1997", American Journal of Obstetric Gynecology Jan. 2003, 188; 108-115.

Kulakov, V.I. et al., "Operative Gynecology a Manual for Physicians", The NGMA Publishing House, 1998, pp. 306-307.

International Search Report issued Feb. 11, 2004, in connection with International Patent Application No. PCT/AU2003/001494.

International Preliminary Examination Report, issued Sep. 28, 2004 in connection with International Patent Application No. PCT/AU2003/001494.

Supplemental European Search Report, dated Feb. 29, 2008.

Office Communication, dated Sep. 8, 2009, in response to the Information Disclosure Statement filed Jul. 30, 2009, received in U.S. Appl. No. 10/534,930, filed Dec. 22, 2005.

Notice of Allowance and Fee(s) Due, with Examiner's Amendment, dated Aug. 5, 2009, received in U.S. Appl. No. 10/534,930, filed Dec. 22, 2005.

Amendment After Final, dated Jun. 29, 2009, in response to the Office Action dated Mar. 5, 2009, received in U.S. Appl. No. 10/534,930, filed Dec. 22, 2005.

Interview Summary, dated Jun. 23, 2009, referring to interview of Jun. 17, 2009, regarding U.S. Appl. No. 10/534,930, filed Dec. 22, 2005.

Office Action, dated Mar. 5, 2009, received in U.S. Appl. No. 10/534,930, filed Dec. 22, 2005.

Amendment, dated Dec. 16, 2008, in response to Office Action dated Sep. 18, 2008, received in U.S. Appl. No. 10/534,930, filed Dec. 22, 2005.

Office Action, dated Sep. 18, 2008, received in U.S. Appl. No. 10/534,930, filed Dec. 22, 2005.

Election and Amendment, dated Jun. 26, 2008, in response to Office Action dated May 28, 2008, received in U.S. Appl. No. 10/534,930, filed Dec. 22, 2005.

Office Action, dated May 28, 2008, received in U.S. Appl. No. 10/534,930, filed Dec. 22, 2005.

* cited by examiner

METHOD OF SURGICAL REPAIR OF VAGINA DAMAGED BY PELVIC ORGAN PROLAPSE AND PROSTHETIC MATERIALS AND DEVICES SUITABLE FOR USE THEREIN

CROSS-REFERENCE TO RELATED APPLICATIONS

This application is a divisional of U.S. patent application Ser. No. 10/534,930, filed on Dec. 22, 2005 now U.S. Pat. No. 7,628,155, which is the U.S. national stage of International Patent Application No. PCT/AU2003/001494, filed on Nov. 12, 2003, which, in turn, claimed priority of Australian Patent Application No. 2002952693, filed on Nov. 15, 2002, and Australian Patent Application No. 2003904937, filed on Sep. 10, 2003. The disclosures of the foregoing applications are incorporated by reference herein in their entirety.

FIELD OF THE INVENTION

This invention relates to a method for the surgical repair of a vaginal wall damaged by the prolapse of any one or more of the pelvic organs, various prosthetic materials and devices useful in such surgery and to kits suitable for use by surgeons when treating women suffering from pelvic organ prolapse.

BACKGROUND TO THE INVENTION

In Australia almost one in four women undergo surgery for pelvic organ prolapse. In many other countries the rates are higher. Each year in the USA approximately 200,000 women undergo pelvic organ prolapse surgery. Pelvic organ prolapse generally involves the descent of the uterus, the bladder or the rectum along the vagina towards (or in extreme cases protruding beyond) the introitus. Women of advancing years or those that have borne several children are more frequent sufferers of pelvic organ prolapse.

Traditional vaginal surgery is associated with a high failure rate. It is between 30-40%. Complex and elaborate abdominal, vaginal and laparoscopic procedures such as abdominal sacral colpopexy, transvaginal sacrospinous ligament fixation and laparoscopic sacral colpopexy have been developed to reduce the risk of prolapse recurrence. Unfortunately these procedures require a high level of surgical expertise and are only available to a small number of specialist practitioners and therefore to a small number of patients. Details of various procedures currently in use are described in Boyles S H., Weber A M, Meyn L.—"Procedures for pelvic organ prolapse in the United States", 1979-1997. American Journal of Obstetric Gynaecology 2003, 188; 108-115.

More recently there has been a trend towards the use of reinforcing materials to support a vaginal wall damaged by prolapse. Prosthetic materials such as donor fascia lata, pig dermis and various types of synthetic mesh have been utilized with mixed success. These materials are generally positioned under the vaginal wall or walls and sutured into position. The applicant has recognized that the synthetic meshes currently in use are far from ideal as they have been designed principally for the treatment of anterior abdominal wall herniation and are generally too heavy for the treatment of genital prolapse. Some of the meshes in current use are associated with long term problems which include pain with sexual intercourse, erosion of the mesh into the lumen of the vagina (this requires surgery to remedy) and shrinkage of the mesh.

It is an object of the present invention to provide a simplified surgical procedure suitable for treatment of different forms of pelvic organ prolapse. It is a further object to provide an improved prosthetic material and device suitable for use in vaginal repair in the treatment of pelvic organ prolapse.

SUMMARY OF THE INVENTION

In accordance with the first aspect of the present invention there is provided a method for repairing a vaginal wall which has been damaged by one or more prolapsed pelvic organs, said method including:
 (a) mobilising the vaginal epithelium off the underlying fascia of at least a portion of the damaged vaginal wall;
 (b) positioning a prosthetic material over the exposed fascia;
 (c) re-fixing the vaginal epithelium over the prosthetic material and the fascia; and thereafter
 (d) locating an intra-vaginal splint into the vagina.

In this description of the method of the invention and elsewhere in this specification (including the claims) the phrase "intra-vaginal splint" means any device sized to be located in the lumen of the vagina and which, once located in the lumen of the vagina, will reduce the mobility of the vaginal walls.

Preferably the prosthetic material once positioned over the exposed fascia is attached to the fascia. Such attachment is usually achieved by sutures, but other methods may be utilised such as by the application of adhesives or surgical staples.

In some cases of prolapse, repair is required to only one of the vaginal walls. However, in many cases of prolapse, repair is required to the anterior and posterior walls of the vagina. In such cases it is not important whether the anterior or posterior wall is repaired first, although it is usually convenient to repair the anterior wall first. Thus, in accordance with the present invention, if both vaginal walls are to be repaired, an intra-vaginal splint is located in the vagina after prosthetic material has been positioned over the fascias of both the anterior and posterior vaginal walls and the vaginal epithelium of both respective walls has been re-fixed over the prosthetic material and the fascias.

Therefore, in the case where both the anterior and posterior vaginal walls are being repaired the preferred method of the invention includes the following steps:
 (a) mobilising the vaginal epithelium off the underlying fascia of at least a portion of the anterior vaginal wall;
 (b) positioning a first prosthetic material over the exposed fascia of the anterior vaginal wall;
 (c) re-fixing the vaginal epithelium over the said first prosthetic material and the fascia of the anterior vaginal wall;
 (d) mobilising the vaginal epithelium off the underlying fascia of at least a portion of the posterior vaginal wall;
 (e) positioning a second prosthetic material over the exposed fascia of the posterior vaginal wall;
 (f) re-fixing the vaginal epithelium over the said second prosthetic material and the fascia of the posterior vaginal wall; and thereafter
 (g) locating an intra-vaginal splint into the vagina.

Preferably, the surgery is performed vaginally.

Whether repairing one or both vaginal walls, in most cases the intra-vaginal splint should be removed after the prosthetic material has become incorporated into the vaginal wall tissue. Preferably the intra-vaginal splint remains in position in the vagina for at least 3 weeks following insertion. Most preferably the intra-vaginal splint is removed between 4 to 6 weeks following insertion.

When repairing the anterior vaginal wall, the vaginal epithelium covering the fascia is preferably mobilised by incision and lateral dissection—most desirably dissection is carried out to (or proximate to) the arcus tendineous facia pelvie on both sides. If it is only the anterior vaginal wall that is to be repaired it is preferred that dissection is continued towards the sacrospinous ligaments on both sides. If both the anterior and posterior walls of the vagina are being repaired it is preferred that the dissection of the epithelium of the anterior wall continue through the arcus tendineous fascia pelvie and into the paravaginal space on each side such that the inner aspect of the pubic bone can be palpated. The fascia may be plicated with sutures before the first prosthetic material is positioned over the exposed fascia.

Likewise, when repairing the posterior vaginal wall the underlying fascia (the recto-vaginal septum fascia) may be plicated. The vaginal epithelium covering the posterior wall is preferably mobilised by incision and dissection—laterally to the levator ani muscles on each side and in the upper part of the vagina, in a lateral and cranial direction through the rectal pillars on both sides towards the sacrospinous ligaments on each side.

Any of the conventional prosthetic materials currently in use for the treatment of pelvic organ prolapse can be employed when performing the surgical methods described above. Thus, a xenograft material, such as pig dermis, an allograft or homograft of skin or a synthetic material suitable for reinforcing the vaginal wall might be utilized.

It is preferred however, that the prosthetic material used in the method of the present invention be a synthetic mesh. More particularly it is preferred that the prosthetic material have the characteristics described below in the description of a new synthetic mesh.

The use of an intra-vaginal splint after the positioning of the prosthetic material has been found by the applicant to result in improved wound healing and a reduced rate of surgical failure. It is preferred that the intra-vaginal splint used in the methods described above have the configuration and characteristics of the new intra-vaginal splint described below.

In accordance with a further aspect of the present invention there is provided a flexible synthetic mesh for use in the repair of a vaginal wall damaged by the prolapse of one or more pelvic organs said synthetic mesh including a plurality of open pores bounded by strands made of non-woven polymeric material, wherein the junctions between the respective strands are without open interstices and wherein a majority of the open pores of the mesh have an area of less than 15 mm$^2$.

Preferably all of the pores of the mesh have an area of less than 15 mm$^2$. Most preferably, the pore size of a majority of the pores of the mesh have an area of less than 10 mm$^2$.

The mesh may be of any suitable shape but generally will incorporate a central body portion and two longitudinal side portions. In the most preferred embodiments the pore size in the central body portion of the mesh is greater than the pore size in the longitudinal side portions. Most preferably the area of each of the pores in the body of the mesh are less than 10 mm$^2$ and the area of each of the pores in the side portions of the mesh will be less than 5 mm$^2$. It is also preferred that the side portions have a width of at least 3 mm. Most preferably the width of the side portions is between 4 and 8 mm.

It is highly desirable that the mesh be light and very flexible. Preferably the mesh has a weight of less than 0.0080 g/cm$^2$. Most preferably its weight is between 0.0020 and 0.0050 g/cm$^2$. Any flexible biocompatible polymeric material may be utilised. The preferred polymeric material is polypropylene and the polypropylene fibres are preferably monofilament fibres.

The mesh of the present invention does not include any open interstices at the junctions between the respective strands. This is important to minimise bacterial growth in or around the mesh after it has been positioned under the virginal epithelium. Thus the mesh will not be woven but instead can be formed by stamping the profile out of a sheet of the polymeric material being used or alternatively, adjacent strands may be connected in a way which does not produce open interstices at the junctions between the respective strands. Most conveniently this is achieved by bonding or welding.

The synthetic mesh of the present invention may be produced in a substantially oval shape for the repair of the anterior vaginal wall and may be substantially trapezium shaped with two extension arms extending upwardly and at an angle away from both side portions of the mesh for repair of the posterior vaginal wall. In a particularly preferred embodiment the oval shaped mesh (intended for use in repairing the anterior vaginal wall) includes two lateral arms, one extending from either side portion of the mesh from the mid section on each side.

When using the preferred oval shaped mesh with lateral arms shaped for repair of the anterior vaginal wall, the mesh is used in the methods described above by being positioned over the pubocervical fascia with each lateral arm placed into a tunnel extending from the anterior vaginal wall dissection to the paravaginal space and the inner aspect of the pubic bone.

The preferred mesh described above for use in the method of the invention for repair of the posterior vaginal wall is positioned over the recto-vaginal septum fascia with each extension arm placed into the tunnel extending from the posterior vaginal wall dissection to the sacrospinous ligament. The mesh is positioned over the fascia and the posterior vaginal wall epithelium is then closed and re-fixed over the mesh to complete the repair.

The prosthetic material, whether it be a preferred synthetic mesh described above or some other suitable material is desirably attached to the respective fascia by using sutures attaching the sides of the prosthetic material to the fascia wall.

Once the vaginal wall or walls have been repaired an intra-vaginal splint is located in the vagina and preferably sutured into position to prevent extrusion. Alternatively the intra-vaginal splint may include lateral spurs. Preferably the intra-vaginal splint is a semi-rigid device and most preferably it is made of a flexible medical grade silicone. As the vagina does not have a universal shape and size it is preferred that the surgeon have available to him at least three differently sized splints so that a splint may be selected which will be appropriate for the patient being treated. Most desirably, a sizing kit will be utilized allowing the surgeon to choose the appropriately sized splint. The sizing kit should comprise at least three differently sized model splints preferably made of medical grade silicone, so that the model splints may be sterilized allowing multiple use. The surgeon will choose the particular sized intra-vaginal splint that matches the corresponding model intra-vaginal splint from the sizing kit, preferably choosing the splint that most comfortably fits into the vagina following the repair whilst contacting both lateral vaginal walls and the superior aspect of the vagina.

In one form, the intra-vaginal splint includes two longitudinally extending side arms both having first and second ends; said side arms being connected at their respective first ends by a first connecting member and at their respective second ends by a second connecting member wherein said first and second connecting members are of different lengths.

Preferably, the connecting members are straight and are parallel with each other. Preferably, the longitudinally extending side arms are straight but are not parallel with each other.

In a most preferred form the intra-vaginal splint is trapezium shaped. The intra-vaginal splint is desirably formed so that the longitudinally extending side arms are disposed in a first plane in the portion of the splint proximate the first connecting member and in a second plane (which is at an angle to the first plane) for the remaining portion of the splint. Preferably the angle between the respective planes is between 8 to 15°. Most desirably it is about 10°.

Preferably the intra-vaginal splint is resilient and bendable about its longitudinal axis so that on application of a bending force the two longitudinally extending side members may be brought into close proximity so that they will be substantially side by side and whereupon release of the bending force will result in the longitudinally extending side arms moving away from each other. This feature facilitates easy insertion of the splint into the vagina.

All or part of the interior of the splint may be closed by a membrane. In one embodiment the membrane is twin skinned and is inflatable so that inflation of the membrane once the intra-vaginal splint is in place will permit the surgeon to tamponade the vagina to prevent and/or control post operative bleeding. This may avoid the need to use a vaginal pack. However, if the surgeon wishes to place a vaginal pack this can be placed around the splint and a urethral catheter can also be placed. Preferably the space between the respective skins or layers of the membrane is in fluid communication with the inside channel of a tube attached to or integrally formed with one of the membrane skins.

The intra-vaginal splint is used to improve wound healing and strength, reduce movement and displacement of the mesh whilst it is becoming incorporated into the vaginal fascial tissues and to avoid the need to use supporting sutures into structures such as the sacrospinous ligament high onto the uterosacral ligaments or paravaginal tissues. Such sutures are often difficult to place and are associated with significant patient morbidity.

In a further aspect of the present invention there is provided a kit suitable for use by surgeons when surgically treating women suffering from pelvic organ prolapse said kit including at least one piece of a flexible synthetic mesh having a plurality of open pores bounded by strands made of non-woven polymeric material in which junctions between the respective strands are without open interstices and wherein a majority of the open pores of the mesh have an area of less than 15 mm$^2$ and one or more differently sized intra-vaginal splints. The flexible synthetic mesh may be provided in a sheet so that appropriately shaped segments can be cut out of the sheet for use in the surgical methods of the invention. Preferably the kit includes a selection of pre-shaped meshes for treatment of both the anterior and posterior vaginal walls in the preferred shapes, pore sizes and configurations as described above. The kit may also include written directions for the use of the components of the kit in accordance with the surgical methods hereinbefore described.

The present invention is hereafter further described by reference to preferred embodiments with reference to the drawings in which:—

Figure 1:
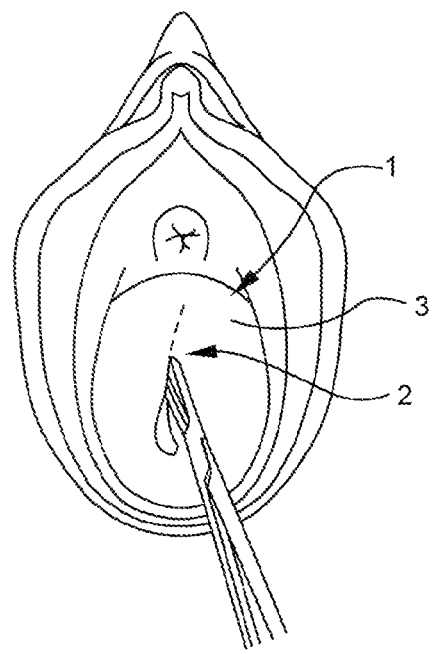
FIG. 1 is a schematic representation of the anterior vaginal wall showing incision into the vaginal epithelium.
Figure 2:
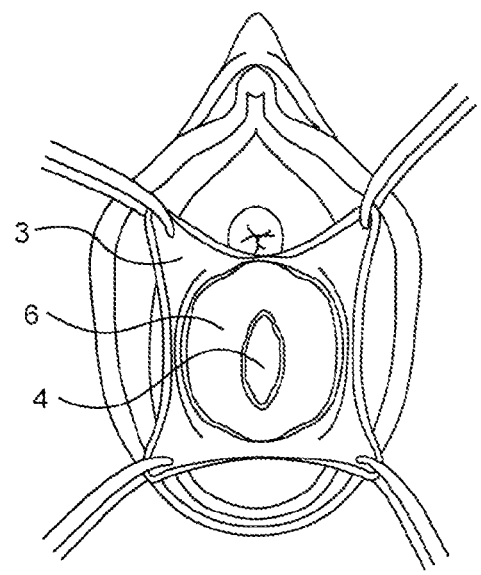
FIG. 2 is a schematic representation of the anterior vaginal wall after mobilisation of the epithelium.
Figure 3:
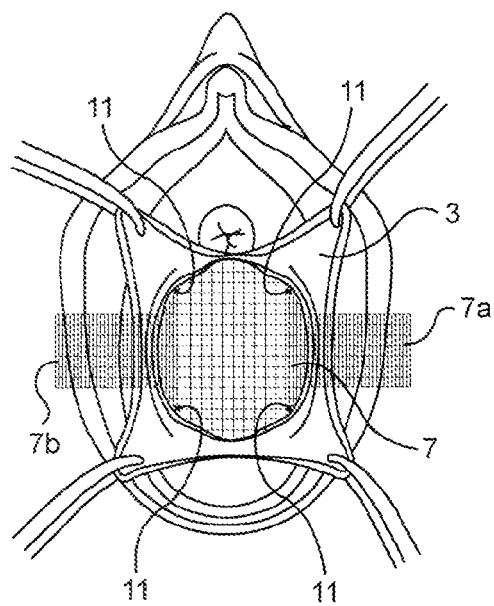
FIG. 3 is a schematic representation of the anterior vaginal wall with mesh positioned over the exposed fascia and sutured into place.
Figure 4:
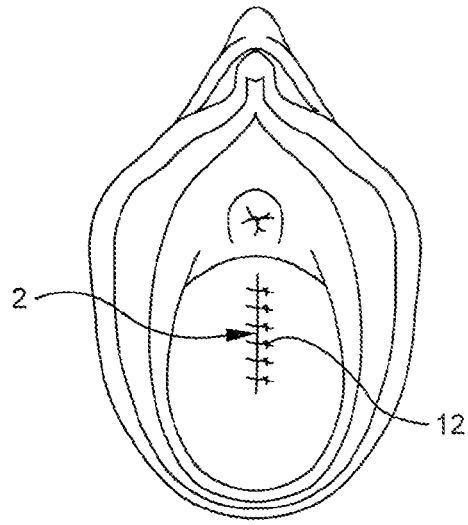
FIG. 4 is a schematic representation of the anterior vaginal wall after the epithelium has been refixed and closed with sutures.
Figure 10:
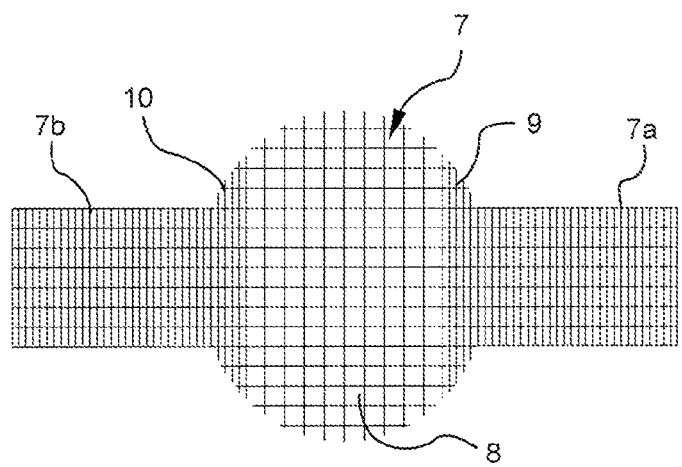
FIG. 10 is a schematic representation of a preferred shape and configuration of a mesh of the present invention for repair of the anterior vaginal wall.

Turning to FIG. 1 there is shown the open vagina (1) and anterior vaginal wall (2). The vaginal wall (2) is covered by an epithelium layer (3). An incision into the vaginal epithelium is shown in FIG. 1. Once the initial incision along the vaginal epithelium layer (3) has been carried out the epithelium (3) is peeled and held away from the fascia (6) as shown in FIG. 2. This lateral dissection is carried out to and then through the arcus tendinous fascia pelvie on both sides, and into the paravaginal spaces on each side. The fascia (6) is preferably plicated (not shown) once the epithelium (3) has been mobilized off the fascia wall. Mesh (7) is then positioned over the defect (4) of the exposed fascia (6). This is with each lateral extension arm (7a, 7b) of the mesh (7) placed into the ipsilateral paravaginal space such that the lateral extension arms (7a, 7b) come into contact with the inner aspect of the pubic bone. The mesh (7) shown in FIG. 3 can be seen in greater detail in FIG. 10. The mesh (7) has a central body portion (8) which is substantially oval in shape and which has top to base longitudinal side portions (9 and 10) which merge into the lateral extension arms (7a, 7b). For most cases a mesh having a dimension of about 50 mm and a width (excluding the lateral extension arms) of between about 30-40 mm will suffice. The lateral extension arms (7a, 7b) in most cases will be about 30 mm long and 20 mm in width. It will be appreciated that the mesh size will depend largely on the dimensions of the vaginal wall being repaired. The mesh shown in FIGS. 3 and 10 is made from polypropylene. In the central body portion (8) of the mesh (7) the area of each of the pores is approximately 9 mm$^2$ (3 mm×3 mm). The side portions (9 and 10) and extension arms (7a, 7b) have a pore size of approximately 3 mm² (1 mm×3 mm). The mesh is made from monofilament polypropylene and is a bonded or welded mesh having a weight of about 0.003 g/cm². Once the mesh (7) has been positioned over the fascia (6) of the anterior vaginal wall (2) it is attached onto the fascia (6) by sutures (11). Excess vaginal epithelium is then trimmed and the anterior vaginal wall is closed by sutures (12) as shown in FIG. 4.

Figure 5:
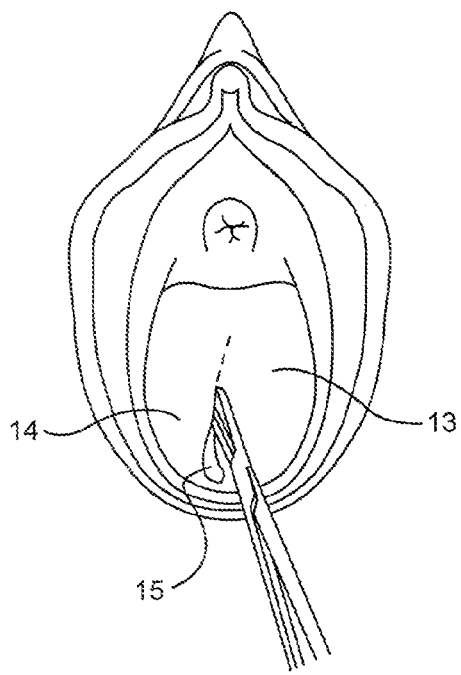
FIG. 5 is a schematic representation of the posterior vaginal wall showing incision into the epithelium.
Figure 6:
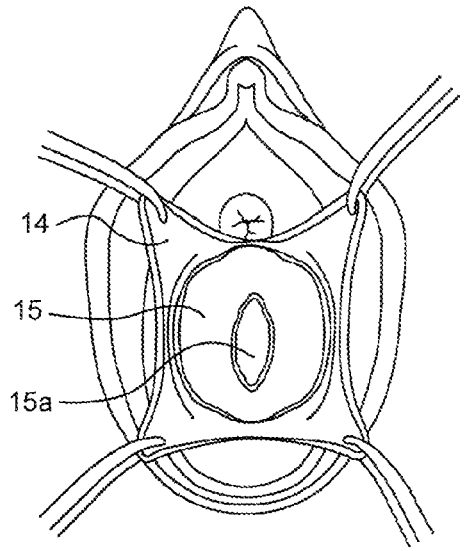
FIG. 6 is a schematic representation of the posterior vaginal wall after mobilisation of the vaginal epithelium.
Figure 7:
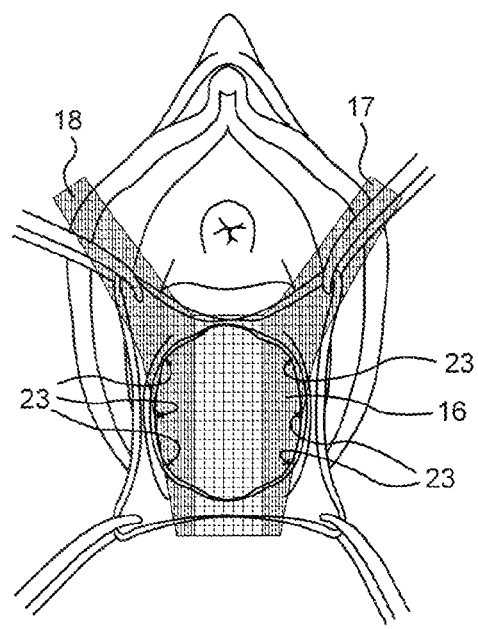
FIG. 7 is a schematic representation of the posterior vaginal wall with mesh positioned over the exposed fascia and sutured into place.
Figure 8:
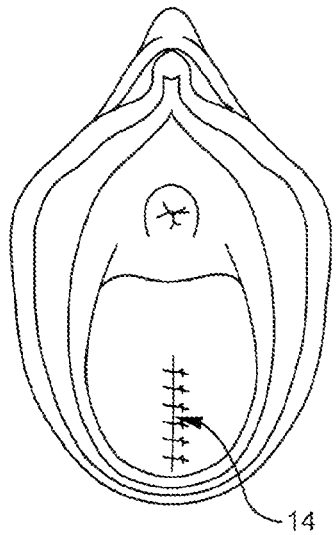
FIG. 8 is a schematic representation of the posterior vaginal wall after the epithelium has been refixed and closed with sutures.
Figure 9:
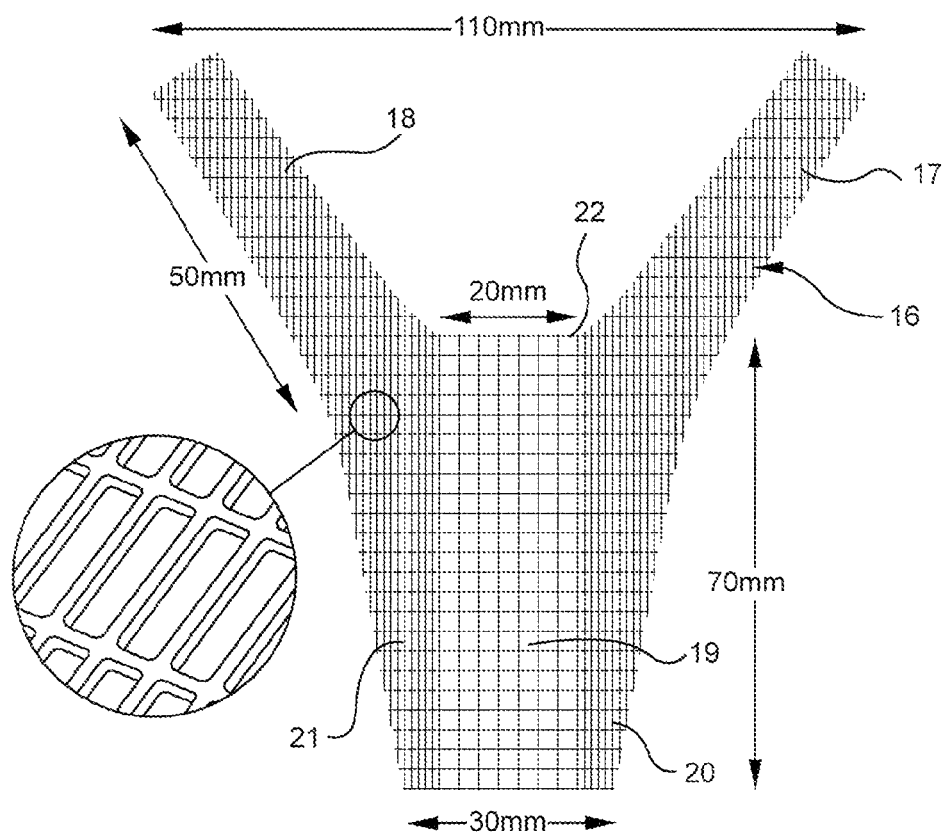
FIG. 9 is a schematic representation of a preferred shape and configuration of a mesh of the present invention for repair of the posterior vaginal wall.
Figure 19:
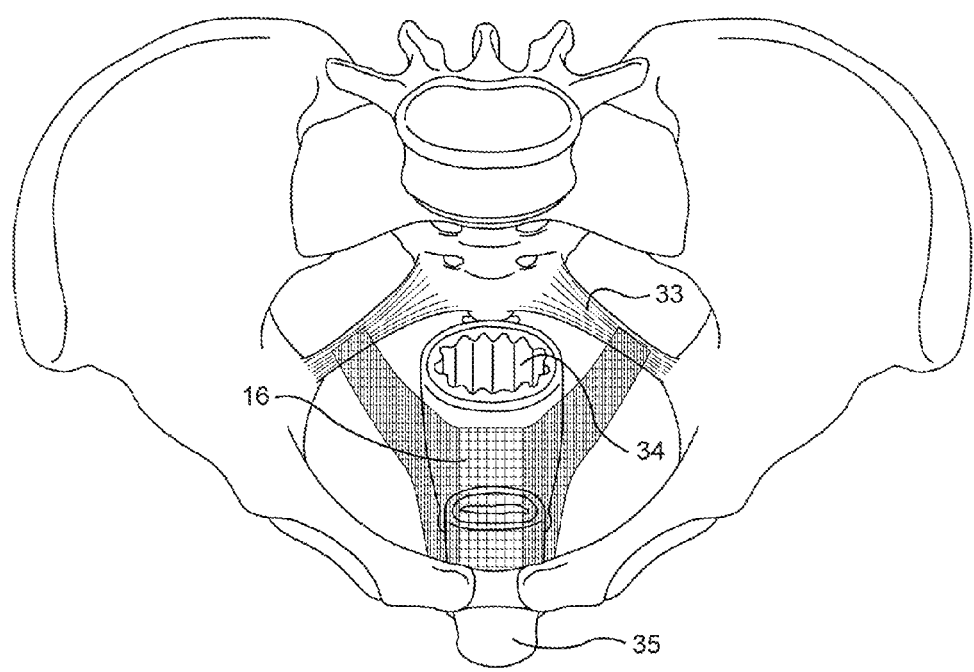
FIG. 19 is a schematic representation showing the positioning of a mesh reinforcing the posterior vaginal wall.

Repair of the posterior vaginal wall is shown in FIGS. 5 to 8. In FIG. 5 posterior vaginal wall (13) is shown with the epithelium (14) of the posterior vaginal wall in place. A longitudinal incision is performed in order to mobilise the epithelium (14) off the underlying fascia (15) as shown in FIG. 5. The defect 15a in fascia 15 is illustrated in FIG. 6. Dissection is carried out laterally to the levator ani muscles on each side. This is also depicted in FIG. 6. In the upper part of the vagina, dissection is continued in a lateral and cranial direction through the rectal pillars on both sides towards the sacrospinous ligaments on each side. This forms bilateral tunnels from the posterior vaginal wall dissection to each sacrospinous ligament. The fascia of the recto-vaginal septum is preferably plicated (not shown). The pre-shaped mesh (16) designed for the posterior vaginal wall repair is shown in FIGS. 7 and 9. It is placed over the recto-vaginal septum facia (15) with each extension arm (17, 18) placed into the tunnel extending from the posterior vaginal wall dissection to the sacrospinous ligament. The positioning of the mesh (16) is more clearly depicted in FIG. 19 which shows its location relative to the sacrospinous ligament (33), the rectum (34) and the vagina (35). Turning to FIG. 9 it can be seen that the pre-shaped mesh (16) designed for the posterior vaginal wall (13) repair has a central body portion (19) and longitudinal side portions (20) and (21). The width of this mesh varies from about 3 cm at the base to 11 cm at the top. The width at the top (22) of the central body portion (19) of the mesh (16) is about 6 cm. The midline length of the mesh (16) is about 7 cm and the length of each extension arm (17, 18) is about 5 cm with a width of about 1.5 cm. Again the mesh (16) is made from monofilament polypropylene and is a bonded or welded mesh having a weight of about 0.0030 g/cm². The area of the pore size of each of the pores of the central body portion (19) of the mesh is approximately 9 mm² (3×3 mm) and at the longitudinal side portions (20,21) approximately 3 mm² (1×3 mm).

Once the mesh (16) has been positioned over the fascia, it is anchored into place by sutures (23) as shown in FIG. 7. Excess posterior vaginal wall epithelium (14) is trimmed and the vaginal epithelium (14) is refixed over mesh (16) as shown in FIG. 8.

Figure 11:
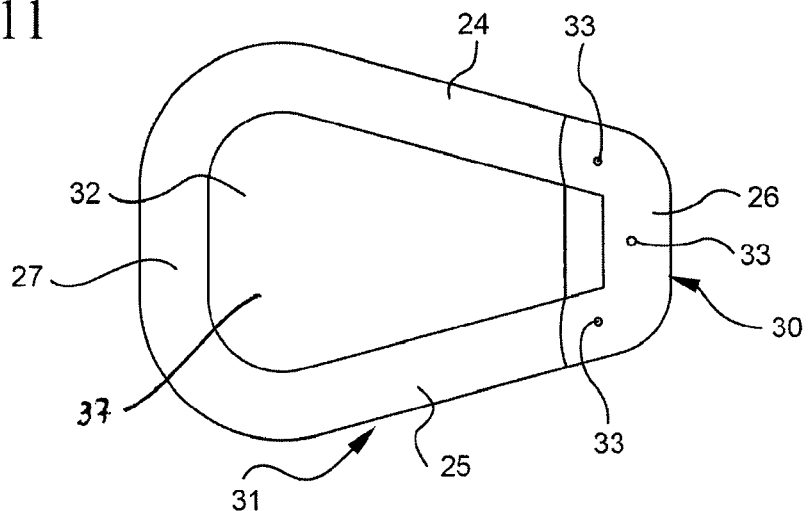
FIG. 11 is a schematic representation of a preferred intra-vaginal splint (top view)
Figure 18:
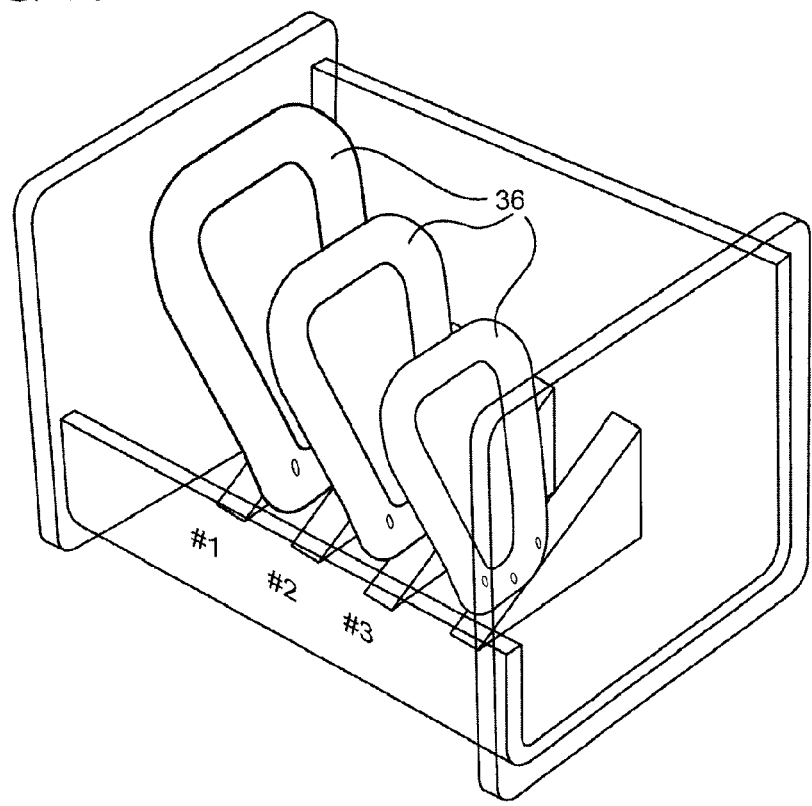
FIG. 18 is a schematic representation of a kit of three differently sized model intra-vaginal splints.
Figure 20:
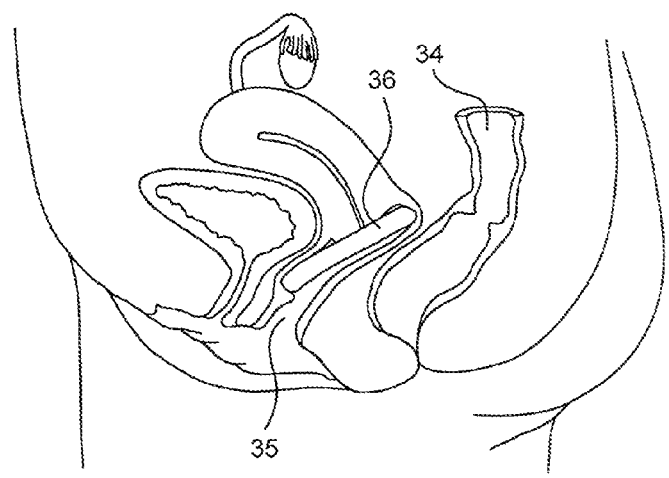
FIG. 20 depicts the intra-vaginal splint once placed within the vagina.

At this point the intra-vaginal splint sizing kit shown in FIG. 18 is used. The surgeon selects from the kit the appropriately sized splint. Once the correct size for the intra-vaginal splint has been determined by using the model splints from the kit, the intra-vaginal splint is inserted into the vagina and sutured into position to prevent extrusion. This is best seen in FIG. 20 where vaginal splint (36) is shown positioned within the vagina (35). The intra-vaginal splint shown in FIG. 11 has small apertures (33) at one end for receiving sutures.

Figure 12:
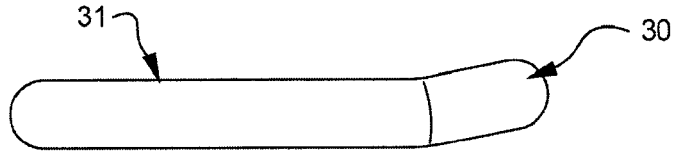
FIG. 12 is a schematic representation of the intra-vaginal splint shown in FIG. 11 (side view)
Figure 13:
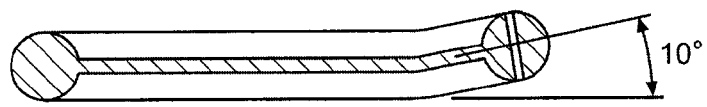
FIG. 13 is a cross-sectioned representation of the intra-vaginal splint shown in FIG. 12 showing the central membrane.
Figure 14:
FIG. 14 is a schematic representation of the intra-vaginal splint shown in FIG. 11 (end view)
Figure 15:
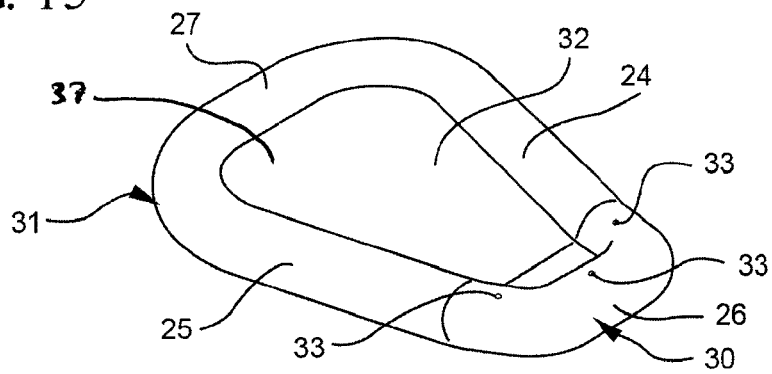
FIG. 15 is a perspective schematic representation of the intra-vaginal splint shown in FIG. 11.
Figure 16:
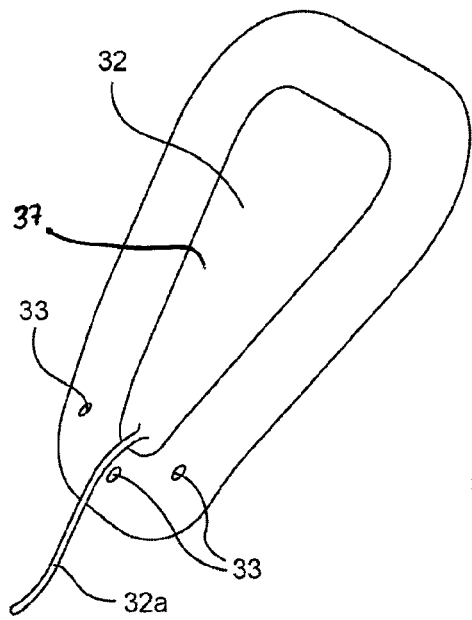
FIG. 16 is a schematic representation of an intra-vaginal splint of the invention incorporating an inflatable membrane.
Figure 17:
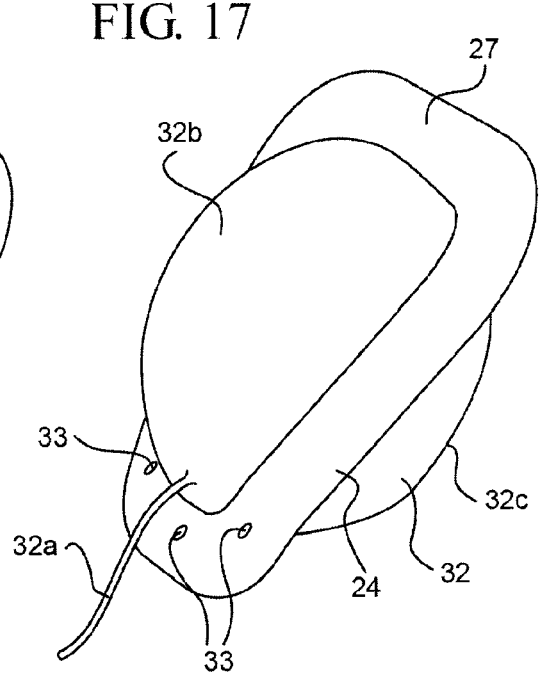
FIG. 17 is a side view of the intra-vaginal splint shown in FIG. 16 with the membrane inflated.

The preferred intra-vaginal splint is shown in FIGS. 11-17. It includes longitudinally extending side arms (24) and (25), and connecting members (26) and (27). The splint has an interior (37) defined by the arrangement of the side arms (24) and (25) and the connecting members (26) and (27). Preferably the base (30) of the splint (that section extending about 20 mm from the connecting member (26)) is inclined at about 10° from the remaining portion (31) of the splint. This is best seen in FIGS. 12 and 13. The central part of the splint is closed by a silicone membrane (32). In one embodiment the membrane is twin-skinned and is inflatable (see FIG. 16). Inflation of the membrane with fluid is possible through tube 32a, which provides a fluid channel into the space between the respective layers 32b and 32c of the membrane 32. This is shown in FIG. 16 (perspective view) and FIG. 17 (side view).

The intra-vaginal splint is preferably retained in the vagina for a period of four weeks. Once this period has elapsed the splint can be removed by which time the synthetic mesh should have become incorporated into the tissue of each of the respective vaginal walls.

Clinical Trial Results

The method of the invention has been the subject of a clinical trial involving 49 women. The mean age of the women was 57.7 years (range 34-79) and mean parity of 2.8 (range 1-6). Twenty-two women (45%) had undergone a prior hysterectomy and 21 (43%) at least one surgical procedure for pelvic organ prolapse. Nine women (18%) had undergone surgery for stress incontinence and five (10.2%) women had undergone two or more operations for pelvic organ prolapse.

The operations performed on the 49 women are detailed in Table 1 set out below. A synthetic mesh was used for the anterior vaginal repair only in 5 women, posterior vaginal repair only in 32 women and both anterior and posterior repairs in 12 women.

When mesh was used in the anterior vaginal repair only, the vaginal epithelium was dissected off the underlying fascia. Laterally, dissection continued until each arcus tendineus fascia pelvis was reached. Superior and lateral, dissection continued until each sacrospinous ligament was reached. A Y-shaped piece of synthetic mesh was placed over the fascia with the extension arms of the mesh being placed in the tunnels created by the dissection onto the sacrospinous ligaments. Sutures were not placed in the sacrospinous ligaments. The mesh was placed loosely and fixed in place with two to three sutures securing the mesh onto the fascia. Excess vaginal epithelium was removed and the epithelium closed over the mesh.

When mesh was used to reinforce the posterior vaginal repair, the vaginal epithelium was dissected off the underlying fascia. Dissection continued laterally on each side to the levator ani muscles. Superior and lateral, the dissection continued through the rectal pillars to each sacrospinous ligament. A "Y-shaped" piece of mesh was placed over the fascia with the extension arms of the mesh being placed in the tunnels created by the dissection onto the sacrospinous ligaments so that the mesh abutted each sacrospinous ligament. Sutures were not placed into the sacrospinous ligaments. Excess epithelium was removed and the posterior vaginal wall epithelium closed over the mesh.

When mesh was used for to reinforce both anterior and posterior vaginal walls, the mesh was placed under the posterior vaginal wall epithelium as described above. The placement of mesh under the anterior vaginal wall epithelium differed from the technique described above. Lateral dissection was continued through each arcus tendineus fascia pelvi into right and left paravaginal spaces so the inner aspect of the pubic bone could be palpated. Anteriorly, there was no dissection onto the sacrospinous ligaments. A "cross-shaped" piece of mesh was cut and placed over the fascia with the extension arms being placed into each paravaginal space so that the mesh abutted the inner aspect of the pubic bone on each side.

All patients received prophylactic antibiotic therapy that was continued for 48 hours following surgery. Clexane was routinely used in each patient and continued until the patient was discharged from hospital.

At the completion of surgery an appropriately sized intravaginal splint was placed in the vagina and sutured in place to prevent dislodgement. The vaginal splint was made of medical grade silicone and three sizes were used for the purposes of sizing. After the patient was discharged, the first review was at four weeks to remove the intra-vaginal splint in the consulting room. By four weeks the sutures holding the vaginal splint in place had dissolved.

Results

Patients were reviewed four weeks following surgery to remove the vaginal splint. No woman had developed further symptomatic or objective evidence of grade 2 (Baden-Walker classification) or more pelvic organ prolapse. No major intra-operative or postoperative complications occurred.

Discussion

Following surgery for pelvic organ prolapse the repair is exposed to rises in intra-abdominal pressure as the patient mobilizes or with coughing, vomiting and straining with bowel evacuation. Potentially, rises in intra-abdominal pressure may adversely effect the healing of the vaginal repair leading to surgical failure and recurrent prolapse. By reinforcing the vaginal repair with mesh and supporting the vagina with a splinting device for four weeks following surgery the risk of surgical failure and recurrent pelvic organ prolapse has been reduced. Mesh is incorporated into the body tissues at three weeks. The vaginal splinting device not only supports the vaginal tissues after surgery but also supports the position of the mesh. By supporting the position of the mesh until incorporation into the body tissues occurs it is possible to avoid placing sutures into the sacrospinous ligaments or paravaginal spaces. This makes surgery much simpler to perform and avoids the specific complications, which can occur with suture placement into these structures.

This procedure is sufficiently simple for general gynaecologists, urogynaecologists and urologists to perform.

TABLE 1

Details of surgery performed for pelvic organ prolapse

| Surgery | Cases (n) |
| --- | --- |
| Surgery using mesh | |
| Anterior repair | 5 |
| Posterior repair | 32 |
| Anterior & posterior repair with mesh | 12 |
| Additional Surgical Procedures | |
| Anterior repair without mesh | 7 |
| Posterior repair without mesh | 1 |
| TVT | 10 |
| Laparoscopic colposuspension | 13 |
| Laparoscopic paravaginal repair | 14 |
| Vaginal hysterectomy | 11 |
| Laparoscopic sacral hysteropexy | 3 |
| Urethral reconstruction | 1 |
| Transvaginal urethrolysis | 2 |
| Martius graft | 1 |
| Laparoscopic tubal ligation | 1 |
| Laparoscopic oophorectomy | 1 |
| Laparoscopic adhesiolysis | 1 |
| Vaginoplasty for vaginal stenosis | 1 |
| Anal sphincter repair | 3 |

The present invention involves a simplified procedure for the treatment of pelvic organ prolapse and vaginal repair. The meshes described are significantly better suited for vaginal surgery as compared with meshes available in the past and in current use and the surgical method enables surgeons to treat prolapse without using complex abdominal, vaginal or laparoscopic procedures.

The invention claimed is:

1. An intravaginal splint, comprising:
    first and second longitudinally extending side arms, each of said side arms having respective first and second ends;
    a first connecting member connecting the respective first ends of said side arms;
    a second connecting member connecting the respective second ends of said side arms, wherein said first and second connecting members are of different lengths and said side arms and connecting members define an interior of said splint; and
    an inflatable twin-skinned membrane for controlling bleeding associated with a surgical site within a vagina, said inflatable twin-skinned membrane at least partially covering said interior of said splint.

2. The intra-vaginal splint of claim 1, wherein said splint comprises a flexible medical grade silicone.

3. The intra-vaginal splint of claim 1, wherein said splint is substantially trapezium shaped.

4. The intra-vaginal splint of claim 1, wherein respective first portions of said first and second longitudinally extending side arms proximate said first connecting member are disposed in a first plane and respective second portions of said first and second longitudinally extending side arms proximate said second connecting member are disposed in a second plane which is oriented at an angle to the first plane.

5. The intra-vaginal splint of claim 4, wherein the angle between the first and second planes is in the range of about 8 to about 15°.

6. The intra-vaginal splint of claim 5, wherein the angle between the respective planes is about 10°.

7. The intra-vaginal splint of claim 1, in combination with at least one piece of flexible synthetic mesh.

8. The combination of claim 7, wherein said at least one piece of flexible synthetic mesh includes a piece of a first flexible synthetic mesh having a substantially oval-shaped portion with a first lateral arm extending from a first side of said oval-shaped portion and a second lateral arm extending from a second side of said oval-shaped portion, said second side being substantially opposed to said first side, and a piece of a second flexible synthetic mesh having a substantially trapezium-shaped portion with a respective first lateral arm extending from a respective first side of said trapezium-shaped portion and a respective second lateral arm extending from a respective second side of said trapezium-shaped portion, said respective second side being substantially opposed to said respective first side.

9. The combination of claim 8, wherein said first flexible synthetic mesh and said second flexible synthetic mesh are of the same type of flexible synthetic mesh.

10. The combination of claim 7, further comprising written instructions for using said at least one piece of flexible synthetic mesh and said intra-vaginal splint in a method for repairing a vaginal wall which has been damaged by one or more prolapsed organs, the method including the steps of (a) mobilizing the vaginal epithelium off the underlying fascia of at least a portion of the damaged vaginal wall, (b) positioning said at least one piece of flexible synthetic mesh over the exposed fascia, (c) re-fixing the vaginal epithelium over said at least one piece of flexible synthetic mesh and the fascia, and thereafter locating one of said intra-vaginal splints into the vagina such that said intra-vaginal splint supports the vaginal wall and prevents substantial movement and displacement of said at least one piece of flexible synthetic mesh while the re-fixed vaginal epithelium heals.

11. The combination of claim 7, wherein said flexible mesh has a plurality of open pores bounded by strands of non-woven polymeric material, respective ones of said strands being connected one to another by junctions, at least a majority of said junctions having no open interstices, wherein at least a majority of the open pores of said plurality of open pores individually have respective areas of less than 15 mm$^2$.

12. The combination of claim 7, further comprising a second intra-vaginal splint having respective first and second longitudinally extending side arms, each of said side arms of said second splint having respective first and second ends, a first connecting member connecting the respective first ends of said side arms of said second splint and a second connecting member connecting the respective second ends of said side arms of said second splint, wherein said first and second connecting members of said second splint are of different lengths than each other and said second splint is of a different size than said splint of claim 1.

13. The intravaginal splint of claim 1, wherein said first and second longitudinally extending side arms are resiliently bendable, such that said side arms bend and move inward toward each other and into close proximity to each other upon application of a bending force to said side arms and said side arms unbend and move outward from each other upon release of the bending force.

14. The intravaginal splint of claim 1, further comprising apertures arranged to receive sutures in one of said connecting members.

15. The intravaginal splint of claim 1, wherein said twin-skinned membrane is attached to at least one of said side arms.

16. The intravaginal splint of claim 1, wherein said twin-skinned membrane is attached to at least one of said connecting members.

* * * * *